United States Patent [19]
Galli et al.

[11] Patent Number: 5,328,838
[45] Date of Patent: Jul. 12, 1994

[54] METHOD FOR IDENTIFYING AND/OR ISOLATING GENES WHICH CODE FOR MEMBRANE RECEPTORS

[75] Inventors: Gabriella Galli; Rafaele Matteoni, both of Rome, Italy

[73] Assignee: Enichem Partecipazioni S.p.A., Milan, Italy

[21] Appl. No.: 755,744

[22] Filed: Sep. 6, 1991

[30] Foreign Application Priority Data

Sep. 7, 1990 [IT] Italy ............................... 21402 A/90

[51] Int. Cl.$^5$ ............................................. C12N 15/10
[52] U.S. Cl. ................... 435/172.3; 435/69.1; 436/501; 536/23.5
[58] Field of Search ........................... 435/69.1, 172.3

[56] References Cited
PUBLICATIONS

P.N.A.S. 80:1194–1198, Mar. 1983, Young et al. Efficient isolation of genes by using antibody probes.
P.N.A.S. 85:7551–7555, Oct. 1988, Marullo et al. Human $B_2$ Adrenagic Receptors Expressed in Escherchia coli Membranes Retain Their Pharmacological Properties.

*Primary Examiner*—Robert J. Hill, Jr.
*Assistant Examiner*—John D. Ulm
*Attorney, Agent, or Firm*—Oblon, Spivak, McClelland, Maier & Neustadt

[57] ABSTRACT

A method for the analysis and isolation of genes which express membrane receptors was developed. Cells of *E. coli* transformed with proper vectors, from phage, as well as from plasmids, containing the cDNA coding for human $\beta$-adrenergic receptors, are grown on slabs of LB/agar; the bacterial colonies, once transferred onto nitrocellulose filters, show specific activity for ($^{125}$I)-iodocyanopindolol (ICYP). The $\beta$-adrenergic receptors expressed in bacteria retain their pharmacologic characteristics after being transferred on filters.

4 Claims, 4 Drawing Sheets

METHOD FOR IDENTIFYING AND/OR ISOLATING GENES WHICH CODE FOR MEMBRANE RECEPTORS

FIELD OF THE INVENTION

The present invention relates to an improved method for identifying and/or isolating recombinant clones which code for the genes of membrane receptors, which method exploits the functional expression of receptors in *E. coli* and their interaction with specific ligands and is substantially based on the replication on filters of the bacterial colonies and on their labeling with radioactive ligands; the invention relates in particular to a method for identifying and/or isolating clones coding for human β-adrenergic receptors.

DISCUSSION OF THE BACKGROUND

Several techniques are known for cloning genes. In the mean time, the difficulties met in the attempts to assign a specific function to the cloned genes, are known as well. On the other hand, knowing the genes which compose human DNA is the basic step which has to be coped with, if one just wishes to hope to be able to diagnose at the right time and hence properly treat a very large number of diseases, which, still to date, are regarded as hopeless.

Human genes are very numerous (they are thought to be in a number of the order of 100,000) and each of them performs a particular task: from one gene the colour of the eyes, and from another gene the blood group depend; from the genes also the hereditary diseases depend, as well as the arising and transmission of certain tumoral forms.

Identifying the individual genes is therefore of interest for the biologist, the physician, and all those who from such a knowledge should draw, as said, suggestions for diagnoses and treatment therapies with the preparation of the relevant kits and medicines.

It is well-known that the nucleotidic sequence can be used to predict which protein a cloned gene will encode, and can suggest the class to which the protein could belong, but, in general, the problem of the identification of the function of a cloned gene is still unsolved and to date, in spite of studies carried out in depth worldwide, only a few tens of human genes were identified and isolated.

The present Applicant has found now a method for identifying and/or isolating genes which code for membrane receptors of whatever biological origin, which is much simpler and faster than the analogous methods based on the expression of receptors in eucaryotic cells, and which is extremely useful when addressed to the cloning of the membrane receptors.

The conventional methods for cloning receptors for neurotransmitters require the purification of the receptor, the generation of partial sequences of aminoacids and the use of synthetic oligonucleotides to be used as probes to obtain cDNA or genomic clones: however, in the case of most neurotransmitter receptors, their rarity renders them extremely difficult to purify, and only very seldom has the cloning of receptors by expression been carried out successfully [Masu Y., Nakayama K., Tamaki H., Harada Y., Kuno M., Nakahishi S. (1987) Nature 329 836-838; Julius D., MacDermott A. B., Axel R., Jessel T. M. (1988) Science 241 558-564; Yokota Y., Sasai Y, Tonaka K., Fujiwara T., Tsuchida K., Shigemoto R., Kakizuka A., Okhubo H., Nakanishi S. (1989) J. Biol. Chem. 264 17649-17652; Shigemoto R., Yokota Y., Tsuchida K., Nakanishi S. (1990) J. Biol. Chem. 265 623-628; Tanaka K., Masu M., Nakanishi S. (1990) Neuron 4 843-854].

Functional receptor molecules are obtained as well by microinjecting in vitro synthetized mRNA into oocites of Xenopus, and also some marginal indications exist on the functional expression in *E. coli* of some genes for human receptors [Marullo S., Delavier-Klutchko C., Eshdat Y., Strosberg A. D., Emorine L. (1988) Proc. Natl. Acad. U.S.A. 85 7751-7555]. Unfortunately, none of these reports makes possible a practical technique for identifying and isolating genes endowed with a specific receptor activity to be developed.

The method according to the present invention makes it possible to overcome these limitations, which, to date, have to be ascribed to the technologies known from the prior art and, exploiting the above cited possibility of functional expression of the receptors in *E. coli* and their interaction with specific ligands, makes it possible to identify recombinant clones coding for the genes of said receptors. The present method essentially consists in the replication on filters of the bacterial colonies expressing membrane receptors and their labeling with radioactive ligands.

SUMMARY OF THE INVENTION

In particular, the method for identifying and/or isolating genes coding for human membrane receptors according to the present invention comprises the following operations:

preparing a suitable modified vector by inserting into a known vector the regions coding for the interesting receptor;

by using said modified vector, transforming bacterial cells of *E. coli;* adsorbing the bacterial colonies derived from said transformed bacterial cells on suitably treated filters of nitrocellulose;

incubating said colonies on said filter, with a labeled ligand;

possibly isolating the clone-ligand complex and resolving said complex.

DETAILED DESCRIPTION OF THE PREFERRED EMBODIMENTS

The method for identifying the clones which code for the human adrenergic receptors is explained now in detail. Those skilled in the art will have no difficulties in selecting the optimal conditions for identifying (and isolating) clones coding for other receptors, irrespectively of their biological source, which may also be of vegetable kind, or constituted by bacteria.

Identification of clones coding for human adrenergic receptors

Bacteria were used, which express human β-adrenergic receptors. The regions coding for the human β1- and β2-adrenergic receptor have been inserted into EcoRI site of expression vector λgt11 at the 3' end of the gene of β-galactosidase; the modified vectors obtained in that way were assigned the designations <<λβ1>> and <<λβ2>>, and were used together with λgt11 to infect cells of E. coli belonging to Y1089 strain, in order to obtain three lysogens: [λβ1], [λβ2] and [λgt11].

The same number of [λβ1] and [λgt11] cells were seeded on slabs of LB and were allowed to grow for 20 hours. Another mixture containing a same number of [λβ2] and [λgt11] cells was treated in the same way.

The bacterial colonies were adsorbed on nitrocellulose filters impregnated with isopropyl-β-D-thiogalactoside (IPTG) in order to induce the expression of the corresponding fusion proteins, and the filters were separated into two half-filters. Samples of protein from pig brain and lung, which contain high concentrations of β-adrenergic receptor, were deposited on each half filter, to serve as the internal control. Both portions of each filter were subsequently treated in order to analyse the ICYP binding.

Figure 2A:
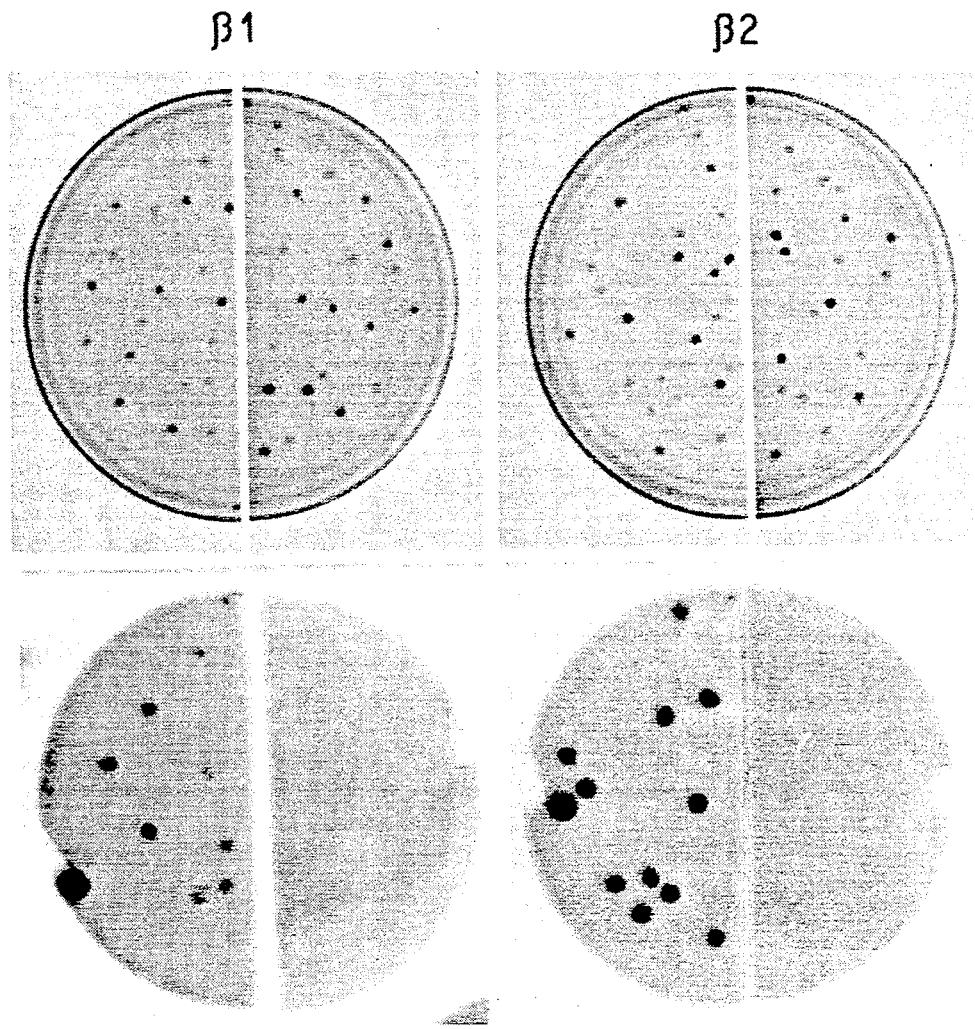
FIGS. 2A and B show a test by replication on nitrocellulose filters of colonies of *E. coli* expressing human β-adrenergic receptors.

FIG. 2A (the left-hand half of each filter) shows that only the bacterial colonies which express β1- or β2-adrenergic receptors are capable of binding ICYP. The addition of non radio-labeled pindolol competes for the bond, thus confirming that said bond is saturable and specific (FIG. 2A, right-hand half of each filter).

The sensibility of the test is so high that, when [λβ2] and [λgt11] cells are mixed in the ratio of 1:1000, one single positive colony can be identified among hundreds of other colonies on the same plate. The average number of active receptors per bacterial cell results to be 23 in [λβ2] cells and 11 in [λgt11] cells (see Table 1).

These values were computed from saturation charts obtaine from bacterial suspensions.

Figure 2B:
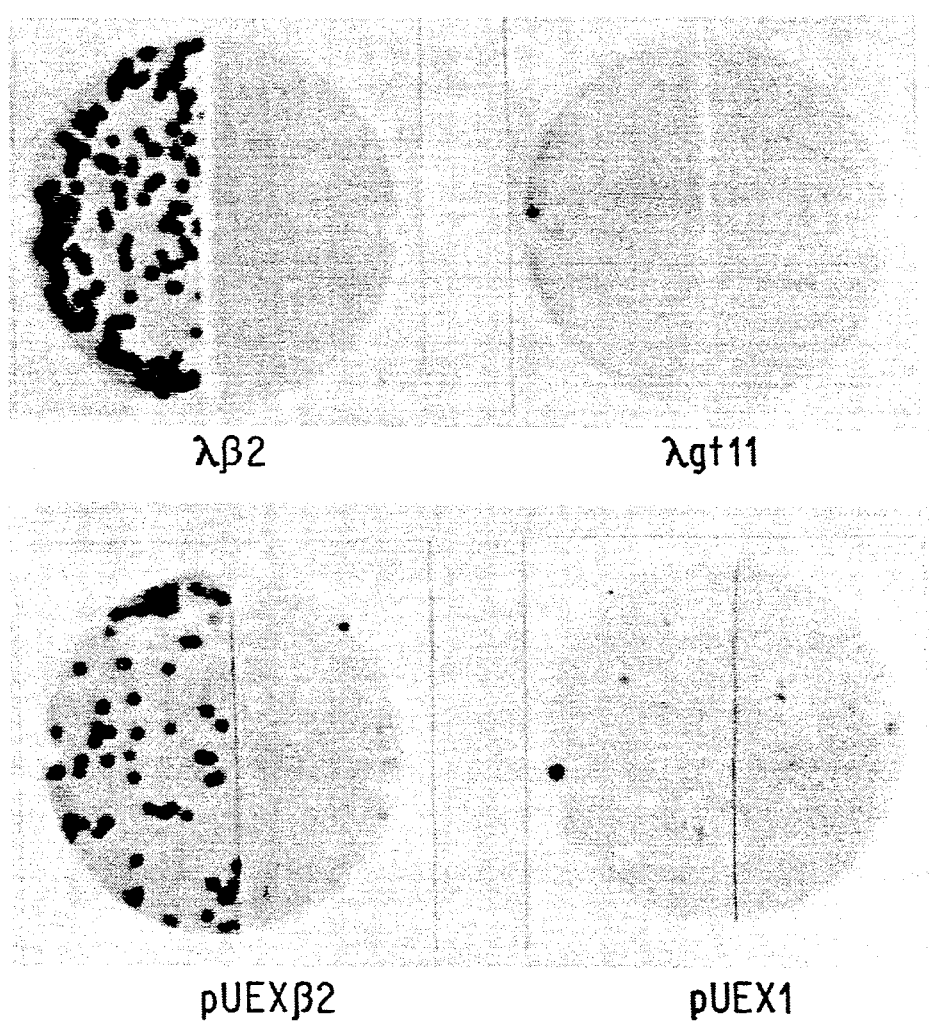

FIG. 2B shows the results obtained from a similar test carried out by replication on a filter of bacterial colonies which express the human β2-adrenergic receptor inserted in the plasmidic pUEX vector, pUEX-β2 plasmid expresses a β-galactosidase-β2-adrenoreceptor fusion protein, producing an average of 13 active receptors per cell (see Table 1).

Figure 3:
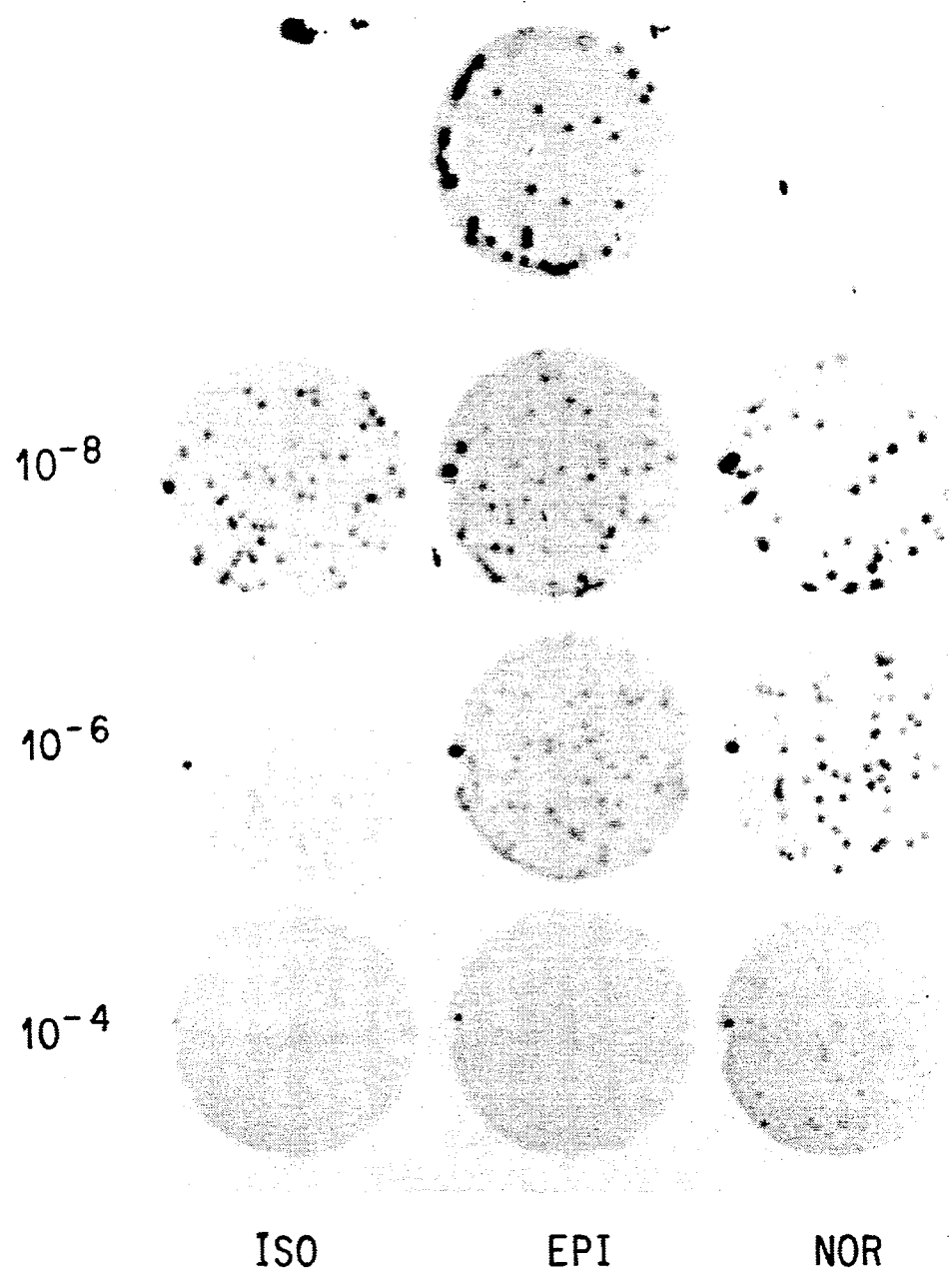
FIG. 3 shows a test by replication on nitrocellulose filters of λβ2 in the presence of different β-adrenergic agonists.

In order to further characterize the specificity of the test by replication on filters, 3 β-adrenergic agonists were tested on [λβ2] cells in bond-competition tests. The bond of ICYP to the bacterial colonies in the presence of said three agonists shows an order of power of competition which is typical for the β2-adrenergic receptor, i.e.:

isoprotenerol > epinephrine > norepinephrine (see FIG. 3).

As already mentioned hereinabove, the novel methodology can be used in order to identify and isolate those genes which code for membrane receptors of any kind. The herein disclosed technique is based on the bond which specific ligands establish with bacterial cells which express the receptors. This method is considerably simpler and faster than similar methods based on the expression of genes for receptors in eucaryotic cells [Machida C.A., Bunzow J., Hanneman E., Grandy D., Civelli D. (1989) DNA 8, 447–455]. Although the effectiveness of this method was only tested for human β1- and β2-aldrenergic receptors, we stress that the same can be used in general for the analysis of gene libraries of expression from cDNA.

The experimental protocol disclosed requires the functional expression of the receptor in question in E. coli, and the availability of specific ligands.

Several examples of functional expression in bacteria, besides human β-adrenergic receptors, were reported in the past in the technical literature.

The functional expression in E. coli of a human receptor, as in the case of adrenergic receptors, suggests that the necessary membrane medium necessary for the correct interaction with specific lignds is retained in the bacteria and that both bacterial and eucaryotic integral membrane receptors share such a trans-membrane organization.

In order to define the topology of a polytopic membrane protein, it is necessary to determine which proteinic domains are situated at both sides of the same membrane.

In E. coli, genic fusions can be used to obtain topologic information. For example, fusions between β-galactosidase and alkaline phosphatase can be used to study the topology of human β-2-adrenergic receptor. The possibility of topologic studies represents one of the advantages of a bacterial expression system for receptor proteins, as compared to systems using mammalian cells in culture.

The analysis of the recombinant receptors requires the availability of ligands with relatively high affinity constants, because only these will be capable of forming complexes with a long enough average life for withstanding the several necessary washes. A wide range of radioiodine-labeled ligands have become available recently. The $K_d$ values of most ligands for receptors couled with G-proteins are of the order of magnitude of $10^{-9}$M, whilst the complex of ICYP with the human β2-adrenergic receptor has a $K_d$ of 10 pM. The use can be hypothesized of such procedures as U.V.-irradiation in order to stabilize by covalent bonds complexes between receptors and ligands endowed with lower affinity.

Designing specific vectors can furthermore contribute to increase the number of active receptor molecules expressed in each bacterial cell.

EXAMPLES Assemblies derived from genes of β-adrenergic receptors

Two fragments, obtained by concomitant digestion with the restriction enzymes BstEII-ApaI and NcoI-PvuII, (respectively of size of 1.4 Kb and 1.6 Kb) from cDNA of human β1- and β2-adrenergic receptors were modified with adapters for EcoRI and were linked in register to the only EcoRI site of lacZ gene of λgt11 phage Cells of Y1089 strain of E. coli were infected with the recombinant phage and the lysogenic phage containing colonies were selected by growth at proper temperatures. The EcoRI fragment of 1.66 Kb of the gene for the human β2-adrenergic receptor was also sub-cloned in register to the single EcoRI site of pUEX1 plasmid, and such an assembly was used in order to transform cells of MC1061 E. coli. The correct translation register of the derived fusion proteins was verified by the sequencing of the corresponding DNA.

The tests by replication on filters of the bacterial colonies expressing human β-adrenergic receptors were carried out as follows:

The bacterial cells were seeded on slabs of LB-agar of 10 cm of diameter and were grown for 12 hours at 30° C. Circular nitrocellulose filters (of 8.5 cm of diameter), previously drenched in 10 mM IPTG in the case of the expression of [λgt11], [λβ1] and [λβ2] lysogens were then laid above the bacterial colonies; the expression of proteins was induced for 2 hours, at 30° C. for the lysogenic colonies, and at 42° C. for the colonies transformed with pUEX1 and pUEXβ2, before the removal of the filters. The subsequent treatments were carried out at room temperature, with constant rocking. The replications on filter of the bacterial colonies were first incubated for 60 minutes in 10 ml of bond-establishing buffer (90 mM NaCl, 10 mM Tris-HCl pH 7.5) containing 20 mg/ml of bovine serumalbumin, and were then transferred for 90 minutes in 10 ml of bond-establishing buffer containing 20 mg/ml of bovine serumalbumin and 20 pM ICYP (2000 Ci/mmol, Amersham, U.K.).

The filters were then washed 4 times for 15 minutes each time, in 10 ml of bond-establishing buffer containing 0.2% Tween 20, were dried at room temperature for 5 minutes, and were then exposed for 6–16 hours, at −70° C., on an autoradiographic plate with intensifier screens.

The studies of competition with non-labeled adrenergic ligands were carried out by adding various concentrations of the competitors during the incubation with ICYP.

Preparation and use of pig brain and lung membranes

The membranes from pig brain and lung were prepared according to the method by Benovic at al. [(1984) Biochemistry 23 4510–4518]. The membranes were resuspended at a protein concentration of 5–10 mg/ml in a buffer containing 50 mM Tris-HCl, pH 7.4, 5 mM EDTA, 100 μM phenylmethylsulfonyl fluoride, 2 μM leupeptin and 50 μg/ml soy bean trypsin inhibitor, were frozen in liquid nitrogen and were stored at −80° C.

The activity of bond by β2-adrenergic receptor was tested with ICYP on membrane preparations [Allen et al. (1988) EMBO J. 7 133–138].

The average specific activity of the brain and lung membrane preparations was of 0.07 pmol/mg and 0.16 pmol/mg of protein, respectively. The protein concentration was determined by using the colourimetric microassay by Bradford, using bovine gamma-globulin as the reference [Bradford H.B. (1976) Anal. Biochem. 72 248-254].

Pig membranes were then used as the positive control in testing the bacterial colonies replicated on filter. After removing the nitrocellulose filters from the agar slabs containing the bacterial colonies, the membranes (0.1-2 μg of total protein in 2-5 μl) were deposited on said filters; the latter were then quickly dried at room temperature, and were used for the test for ICYP binding, as disclosed hereinabove.

The membranes of E. coli from Y090 strain of wild type were prepared as described in the literature.

Figure 1:
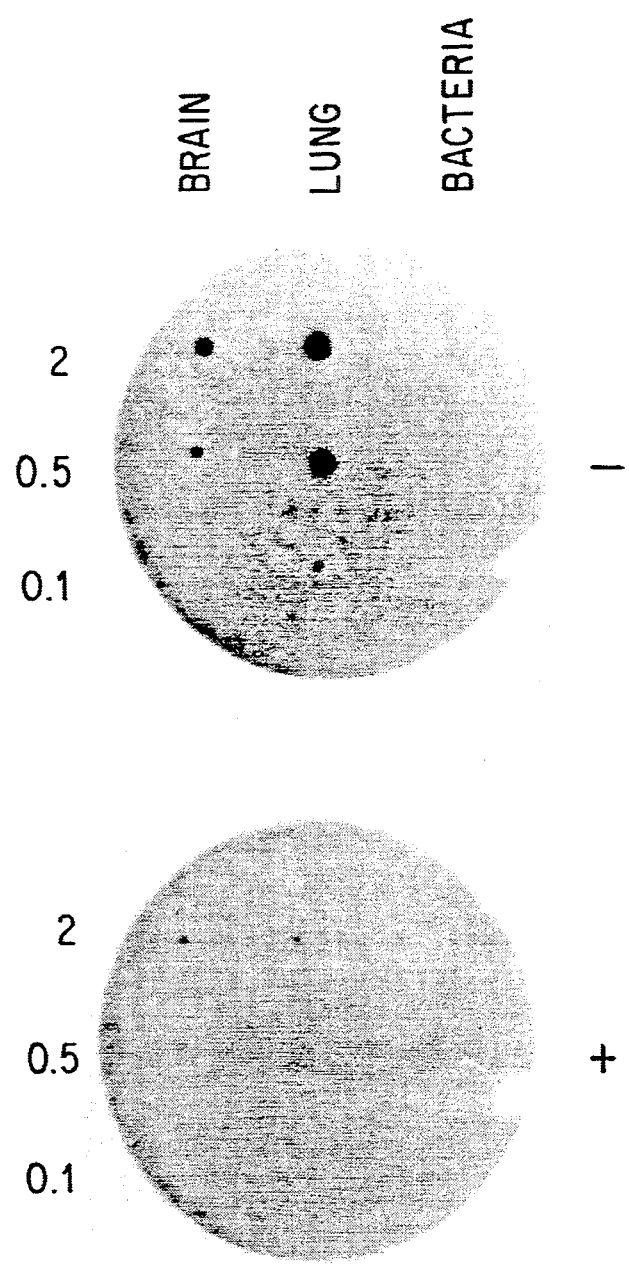
FIG. 1 shows a test for proteins of brain and lung membranes on nitrocellulose filters.

The experimental route disclosed up to here will be better defined from a reading of the figures which accompany the disclosure. An explanation of the figures follows now. FIG. 1. Test by replication on filter of proteins of brain and lung membranes.

Different amounts (0.1, 0.5 and 2 μg) of proteins of pig brain and lung membrane, and from E. coli bacteria of wild type were deposited on nitrocellulose filters; the test for ICYP bond was carried out in the presence (+) and absence (−) of non-labeled competitor (10 μM pindolol). FIG. 2. Test by replication on filter of colonies of E. coli expressing human β-adrenergic receptors (a) A same number of [λβ1] or [λβ2] and [λgt11] colonies were seeded in the presence of X-gal and IPTG on 2 slabs of 10 cm of diameter and were grown at 30° C. for 16 hours. The photographs of both slabs in the upper portion make it possible for the blue colonies, corresponding to [λgt11], to be distinguished from the white colonies, corresponding to [λβ1] and [λβ2]. Both slabs were coated with a nitrocellulose filter drenched with IPTG and were incubated for a further 2 hours at 30° C.; the filters were removed and were cut into 2 half-filters, on each of which proteins of membrane from pig lung were deposited (1 μg). The test for ICYP binding was carried out in the absence (left-hand side of each filter half) or presence (right-hand side of each filter half) of 10 μM non-radiolabeled pindolol. After being washed, the filters were exposed on an autoradiographic film for 14 hours.

(b) The bacterial colonies transformed with the vector of wild type (filters on the right-hand side) and with the vector containing the cDNA for the β2-adrenergic receptor were grown on separate slabs.

FIG. 3. Test by replication on filter of [λβ2] in the presence of different β-adrenergic agonists.

The test for ICYP binding to bacterial colonies transferred on filters was carried out in the absence (top filter) or presence of various concentrations (10−8, 10−8 and 10−4M) of the following non-radiolabeled β-adrenergic ligands: (−)-isoprotenerol, (−)-epinephrine and (−)-norepinephrine.

Table 1. Bond of ICYP to tge bacteria transformed with different vectors expressing β-adrenergic receptors The average number of active receptors per cell was computed from curves of saturation of ICYP bonds in suspensions of bacteria expressing β-adrenergic receptors [Marullo et al. (1988) Proc. Natl. Acad. U.S.A. 85 7751-2555].

The reported values are the average of three independent test runs. The control bacteria (Y1089 cells infected with lgt11 and MC1061 cells transfected with pUEX1) do not show any specific bond activities.

Finally, going back to the disclosure of the method, the following optimum conditions for the functional analysis of the receptors can be outlined:

Samples of membranes of mammalian brain and lung, tissues which contain a high concentration of β-adrenergic receptors [Frielle T. et al. (1987) Proc. Natl. Acad. Sci. U.S.A. 84 7920-7924] were used to determine the optimal conditions for ICYP binding to receptor proteins immobilized on a nitrocellulose filter.

Samples of membranes of pig brain and lung, once adsorbed on filter, specifically bind ICYP (FIG. 1). Three experimental evidences show that the bond is a specific one:

(1) The intensity of the autoradiographic signal appears to be proportional to the amount of protein immobilized on the filter;

(2) The lung membranes show a higher specific activity than brain membranes, as expected on the basis of the matter of fact that lung is provided with a higher concentration of β-adrenergic receptors than brain;

(3) An excess of non-radiolabeled antagonist competes with the radioactive ligand for the bond to the membrane proteins.

FIG. 1 evidences also that preparations of membranes from *E. coli* bacteria of wild type do not show any ICYP binding activity.

Several experimental conditions were tested: the best results were obtained by keeping the proteins replicated on filter in a Tris-NaCl buffer containing 2% bovine serumalbumin for 1 hour, then incubating for 2 hours in the same buffer, in the presence of 20 pM ICYP.

The filters were then washed 4 times in a Tris-HCl buffer containing 0.2% Tween 20.

In the absence of bovine serumalbumin during the pre-incubation and/or incubation with ICYP, a marked reduction occurs in specific bond with membrane preparates. Washing in the presence of a mild detergent (0.2% Tween 20) is necessary in order to decrease the aspecific bond to the nitrocellulose matrix.

TABLE 1

| Vectors | Genes | Active Receptors per cell |
|---|---|---|
| λgt11 | β1 | 11 |
|  | β2 | 23 |
| pUEX1 | β2 | 13 |

We claim:

1. A method for identifying and/or isolating DNA encoding G-coupled membrane receptors, comprising:

preparing a vector encoding a membrane receptor which naturally occurs coupled to a G-protein;

transforming *E. coli* cells using said vector;

adsorbing bacterial colonies derived from said transformed bacterial cells on a filter of nitrocellulose;

incubating said colonies on said filter with a labeled ligand;

identifying those colonies containing said DNA by their ability to bind said ligand;

and, optionally, isolating said DNA.

2. The method of claim 1, comprising:

inserting DNA encoding human β1- or β-2-adrenergic receptor into an EcoRI site of expression vector λgt11 at the end of DNA encoding β-galactosidase;

transforming cells of *E. coli* using the so obtained vector and growing said cells;

adsorbing colonies of transformed *E. coli* on nitrocellulose filters impregnated with isopropyl-β-D-thiogalactosidase;

treating said colonies on said filter with $^{125}$I-iodocyanopindolol.

3. The method of claim 1, wherein said transformed *E. coli* cells belong to strain Y1089.

4. The method according to any one of claims 1, 2, or 3, wherein said vector is pUEX1.

* * * * *